US00RE41745E

(19) United States
(12) Reissued Patent
Bennett

(10) Patent Number: US RE41,745 E
(45) Date of Reissued Patent: Sep. 21, 2010

(54) RECOMBINANT VENEZUELAN EQUINE ENCEPHALITIS VIRUS VACCINE

(75) Inventor: Alice M. Bennett, Salisbury (GB)

(73) Assignee: The Secretary of State for Defence, Defence Evaluation & Research Agency, Hampshire (GB)

(21) Appl. No.: 11/892,970

(22) PCT Filed: May 5, 1999

(86) PCT No.: PCT/GB99/01387

§ 371 (c)(1),
(2), (4) Date: Nov. 28, 2000

(87) PCT Pub. No.: WO99/63098

PCT Pub. Date: Dec. 9, 1999

Related U.S. Patent Documents

Reissue of:
(64) Patent No.: 6,936,257
Issued: Aug. 30, 2005
Appl. No.: 09/701,299
Filed: Nov. 28, 2000

(30) Foreign Application Priority Data

May 29, 1998 (GB) ..... 9811433

(51) Int. Cl.
*C12N 15/63* (2006.01)

(52) U.S. Cl. ..... 424/218.1; 424/184.1; 424/199.1; 424/204.1; 435/69.3; 435/236; 435/320.1

(58) Field of Classification Search ..... None
See application file for complete search history.

(56) References Cited

U.S. PATENT DOCUMENTS 5,185,440 A 2/1993 Davis et al.
5,505,947 A 4/1996 Johnston et al.
6,936,257 B1 8/2005 Bennett

FOREIGN PATENT DOCUMENTS

WO WO 98/53077 11/1998

OTHER PUBLICATIONS

Grieder et al, "Specific Restrictions in the progression of Venezuelan Equine . . . " Virology 206, 1995, pp. 994–1006.
Kinney R M et al.: "Recombinant vaccinia/Venezuelan equine encephalitis (VEE) virus expresses VEE structural proteins." Journal of General Virology, (Dec. 1988) 69 (PT12) 3005–13., pp. 3005–3006, 3007.
Davison, Andrew J. et al.: "Structure of vaccinia virus early promoters" J. Mol. Biol. (1989), 210 (4), 749–69.
Kinney R M et al.: "The full–length nucleotide sequences of the virulent Trinidad donkey strain of venezuelan equine encephalitis virus and its attenuated vaccine derivative, strain TC–83." Virology, (May 1989) 170 (1) 19–30.
Hunt A R et al.: "Localization of a protective epitope on a Venezuelan equine encephalomyelitis (VEE) virus peptide that protects mice from both epizootic and enzootic VEE virus challenge and is immunogenic in horses." Vaccine, (Feb. 1995) 13 (3) 281–8.
Agapov E V et al.: "Localization of four antigenic sites involved in Venezuelan equine encephalomyelitis virus protection." Archives of Virology, (1994) 139 (1–2) 173–81.
Bennett A M et al.: "Improved protection against Venezuelan equine encephalitis by genetic engineering of a recombinant vaccinia virus." Viral Immunology, (1998) 11 (3) 109–17.

*Primary Examiner*—Stacy B Chen
(74) *Attorney, Agent, or Firm*—Nixon & Vanderhye P.C.

(57) ABSTRACT

A prophylactic or therapeutic vaccine for use in protecting mammals such as humans or animals against Venezelan Equine Encephalitis virus (VEE) is described. In particular, the vaccine comprises a recombinant virus such as a recombinant vaccinia virus which is able to express the structural genes of VEE in attenuated form, which has been modified to increase the protective effect of the vaccine. This is achieved by modifying the sequence of the attenuated VEE strain and/or putting this under the control of modified promoter which increases expression from the vector. Formulations of the vaccine as well as methods of treatment using the vaccine are also described.

34 Claims, 4 Drawing Sheets

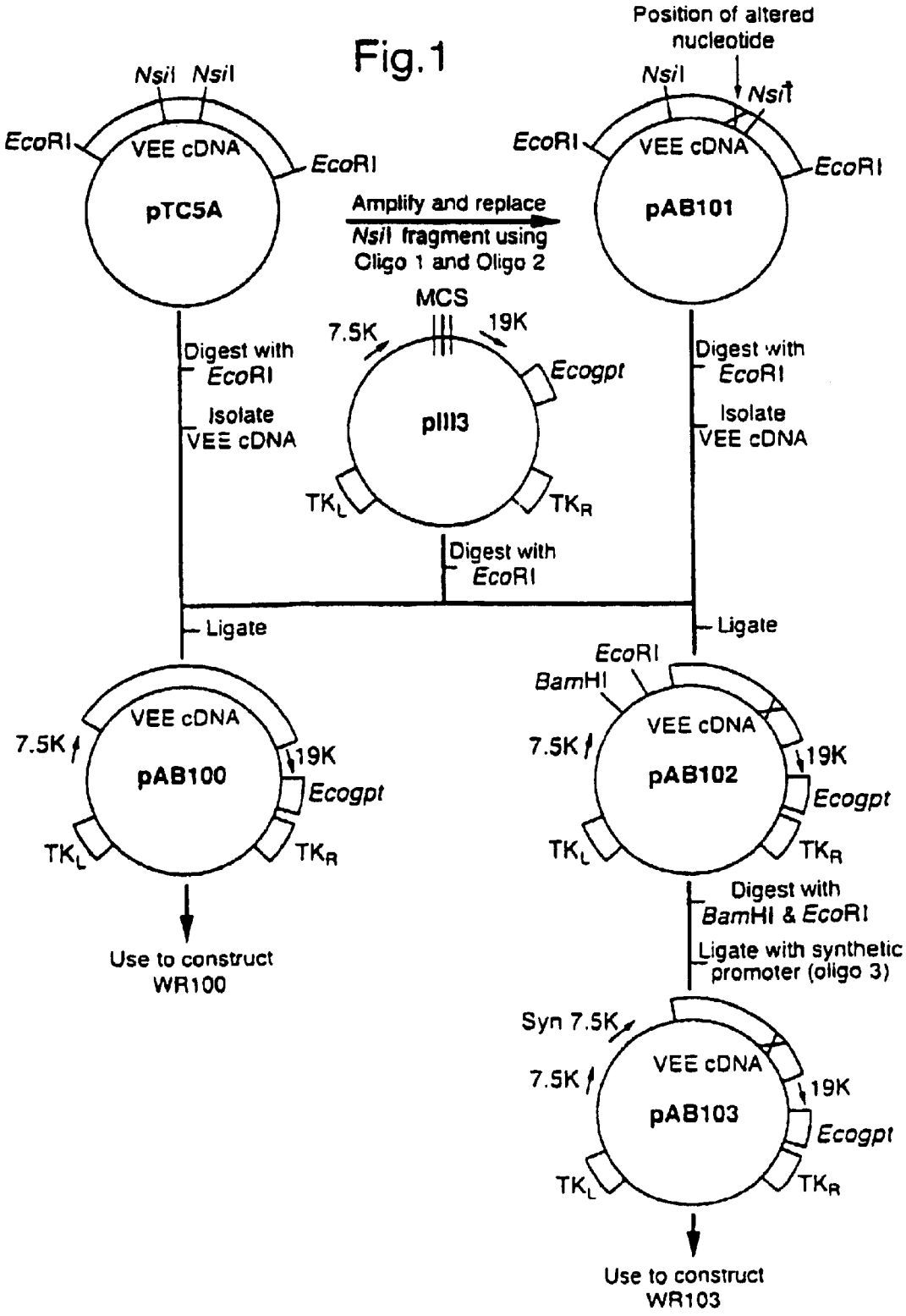
Fig.1
Position of altered nucleotide
NsiI NsiI
EcoRI
VEE cDNA
EcoRI
pTC5A
NsiI
NsiI
EcoRI
VEE cDNA
EcoRI
pAB101
Amplify and replace NsiI fragment using Oligo 1 and Oligo 2
MCS
7.5K
19K
Ecogpt
pIII3
TKL
TKR
Digest with EcoRI
Isolate VEE cDNA
Digest with EcoRI
Isolate VEE cDNA
Digest with EcoRI
Ligate
Ligate
VEE cDNA
7.5K
19K
pAB100
Ecogpt
TKL
TKR
Use to construct WR100
EcoRI
BamHI
VEE cDNA
7.5K
19K
pAB102
Ecogpt
TKL
TKR
Digest with BamHI & EcoRI
Ligate with synthetic promoter (oligo 3)
Syn 7.5K
VEE cDNA
7.5K
19K
pAB103
Ecogpt
TKL
TKR
Use to construct WR103

RECOMBINANT VENEZUELAN EQUINE ENCEPHALITIS VIRUS VACCINE

Matter enclosed in heavy brackets [ ] appears in the original patent but forms no part of this reissue specification; matter printed in italics indicates the additions made by reissue.

The present application is a *re-issue of U.S. Pat. No. 6,936,257, which issued Aug. 30, 2005 and was filed as Ser. No. 09/701,299 on Nov. 28, 2000, Ser. No. 09/701,299 is a* 371 U.S. national phase of PCT/GB99/01387, filed May 5, 1999, which designated the U.S.

The present invention relates to a virus vaccine, specifically a vaccine to Venezuelan equine encephalomyelitis virus (VEE), to its preparation and pharmaceutically acceptable formulations and methods of prophylactic and therapeutic methods of treatment using said vaccine.

VEE virus is a mosquito-borne alphavirus which is an important cause of epidemic disease in humans and of epizootics in horses, donkeys and mules in certain parts of the world, in particular the South Americas.

The existing VEE vaccine, TC-83, was initially produced by attenuation of the Trinidad donkey strain (TRD) of VEE by sequential passage in guinea pig heart cell cultures. However, this vaccine is generally regarded as being inadequate for human vaccination. This is mainly due to the high incidence of side effects in vaccinees and the large proportion of vaccinees who fail to develop neutralising antibodies (Monath et al. 1992, Vaccine Research, 1, 55–68).

A vaccinia-based vaccine against VEE has been constructed (Kinney et al. J. Gen. Virol. 1988, 69, 3005–3013). In this recombinant, 26S RNA encoding structural genes of VEE were inserted into the NYCBH strain of vaccinia. The recombinant virus protected against sub-cutaneous challenge but had limited efficacy against aerosol challenge with VEE.

The virulent Trinidad donkey strain of VEE and the attenuated strain TC-83 have both been cloned and sequenced (R. M. Kinney et al. Virology (1989) 170, 19–30) and the amino acid and nucleotide numbering system used in this reference will be used hereinafter. This work has revealed that there are a number of amino acid changes between TRD and TC-83. The majority (five) of these changes occur within the gene encoding the glycoprotein E2.

The changes have been summarised as follows:

TABLE 1

| change | Nucleotide | | Amino acid | |
|---|---|---|---|---|
| Position | TRD | TC-83 | TRD | TC-83 |
| 22, junction region | A | G | non-coding | |
| 1053, $E_2$-7 | G | U | Lys | Asn |
| 1285, $E_2$-85 | C | U | His | Tyr |
| 1391, $E_2$-120 | C | U | Thr | Arg |
| 1607, $E_2$-192 | U | A | Val | Asp |
| 1866, $E_2$-278 | U | C | none | |
| 1919, $E_2$-296 | C | U | Thr | Ile |
| 2947, $E_1$-161 | U | A | Leu | Ile |
| 3099, $E_1$-211 | A | U | none | |
| 3874, 3'-non-coding region | UU | U | non-coding | |

It has also been shown that the first 25 amino acids of the E2 glycoprotein represents a protective epitope. This region includes a single amino acid change (lys→asp) at amino acid 7 in the TC-83 construct as compared to the TRD strain. A 25 bp synthetic peptide based on the TRD sequence VE2pep01 (TRD), protected more mice from TRD virus challenge than a corresponding TC-83 based peptide (A. R. Hunt et al., Virology, 1990, 179, 701–711). More precise mapping of this epitope has been carried out (A. R Hunt et al., Vaccine 1995, 13, 3, 281–288).

The applicants have found ways of increasing the protectiveness of a vaccine and in particular a vaccinia-based vaccine.

In particular, the applicants have found that the protectiveness of the vaccine may be increased either (a) by restoring the lysine residue at amino acid 7 of the E2 protein and/or (b) by modifying the promoter to increase expression of the protective construct.

Thus, in a first aspect, the present invention provides a vaccine for the therapeutic or prophylactic immunisation against Venezuelan Equine Encephalitis (VEE) virus, said vaccine comprising a vector which includes a sequence which encodes an attenuated form of said virus which is capable of producing a protective immune response, wherein the said sequence is such that the amino acid at position 7 in the E2 protein of VEE is lysine.

Suitably, the attenuated form of the VEE virus comprises a derivative or variant of the TC-83 construct or an immunogenic fragment thereof.

Other attenuated forms may be produced by the skilled person, for example using known techniques such as serial passage through another organism, or by recombinant DNA technology, for instance by inactivating genes associated with the replication or virulence of the virus. The structural gene encoding the E2 glycoprotein or a fragment encoding at least the N-terminal 19 amino acids should be retained in order to retain immunogenicity of the construct.

Suitable fragments of the construct are those which include only some of the structural genes of the VEE peptide or which encode only part of the proteins encoded by said genes, provided the construct encodes sufficient antigenic determinants to ensure that it is capable of producing a protective immune response in a mammal to whom the construct is administered.

As used herein, the term "variant" means that the construct is different to the original strain but that it encodes proteins and/or peptides which are the same or similar to those of wild-type VEE or immunogenic fragments thereof. Thus, the changes in the nucleotide sequence may be silent in that they do not produce amino acid changes as compared to the original strain, or they may produce amino acid changes provided these do not alter function of the construct in terms of its ability to produce a protective immune response against VEE. For example, the construct may encode peptides or proteins which are 60% homologous to the wild-type proteins or peptides, suitably more than 80% homologous and preferably more than 90% homologous to the native protein sequence, and provided they produce antibodies which are cross-reactive with wild-type VEE, the protective effects of the construct may be retained.

"Derivatives" may have broadly similar structures but they are derived by manipulating the original constructs using recombinant DNA technology or chemical modification if appropriate.

The vector may contain the usual expression control functions such as promoters, enhancers and signal sequences, as well as a selection marker in order to allow detection of successful transformants. The selection of these will depend upon the precise nature of the vector chosen and will be known to or readily determinable by a person skilled in the art.

Suitably the vector is a viral vector, for example a vector derived from vaccinia, adenovirus, or herpes simplex virus (HSV) BCG or BCC. It is suitably attenuated itself, to minimise any harmful effects associated with the virus on the host.

Preferably, the vector is derived from vaccinia virus, as it has many properties which make it a suitable vector for vaccination, including its ability to efficiently stimulate humoral as well as cell-mediated immune responses. Vaccinia has proven utility as a vaccine vehicle, following the Smallpox eradication programmes. It provides the potential for multi-valent vaccine construction and for oral administration. There are many attenuated strains currently available.

A suitable selection marker for inclusion in a vaccinia vector is the gpt marker gene.

A VEE vaccine was constructed using a WR strain of vaccinia in this work. Preferably, a more highly attenuated strain of vaccinia which would be more acceptable for use in humans is employed. Such strains include Lister, which was used for wide scale vaccination against smallpox, NYVAC (Tartaglia et al, (1992). AIDS Research and Human Retroviruses 8,1445–1447) which contains specific genome deletions, or MVA (Mayr et al, (1975) Infection 3, 6–14) which is also highly attenuated.

Vaccines based upon viral vectors are suitably formulated for parenteral administration as described above. However, it is possible to formulate such vaccines for oral administration, for example by incorporating the vector into a gut-colonising microorganism such as Salmonella and particularly S. typhimurium.

pTC-5A is a plasmid clone of cDNA encoding the structural genes of VEE virus strain TC-83 (Kinney et al. J. Gen. Virol. (1988) 69, 3005–30130). The VEE cDNA is situated downstream of the vaccinia 7.5K promoter which drives expression of the VEE structural proteins when the plasmid is used to construct recombinant vaccinia viruses. Modified 7.5K vaccinia promoters have previously been prepared (Davison & Moss, J. Mol. Biol. 210, (1989) 749–769). It has been found that certain substitution mutations increase the strength of the promoter. By using synthetic promoters which include substitution mutations, the amount of VEE proteins produced from the recombinant virus was increased.

Thus in a further aspect of the invention, there is provided a vaccine for the therapeutic or prophylactic immunisation against Venezuelan Equine Encephalitis (VEE) virus, said vaccine comprising a vaccinia virus vector which encodes an attenuated form of the VEE virus or a variant or fragment thereof which is capable of producing a protective immune response against VEE virus, expression of the said attenuated VEE virus being under the control of a synthetic 7.5K vaccinia promoter which has been subject to mutation which increases the level of VEE virus protein production as compared to the wild-type 7.5K promoter.

In particular, it has been found that substitution mutations within the 7.5 Kd promoter can be effective. These may be illustrated by the following Table:

Wild-type 7.5K promoter:

TAAAAGTAGAAAATATATTCTAATTTATTGCAC (SEQ ID No 1)

Substitution Mutations (emboldened)

TAAAAATTGAAAATACATTCTAATTTATTGCAC (SEQ ID No 2)

TAAAAATTGAAAATATATTCTAATTTATTGCAC (SEQ ID No 3)

Inclusion of a synthetic 7.5K vaccinia promoter in WR103 has been found to increase expression of the downstream VEE cDNA, leading to a 3.59-fold increase in protein production.

The vaccine may comprise the vector itself but it is suitably formulated as a pharmaceutical composition in combination with a pharmaceutically acceptable carrier or excipient. Such compositions form a further aspect of the invention. The compositions may be in a form suitable for oral or parenteral application.

Suitable carriers are well known in the art and include solid and liquid diluents, for example, water, saline or aqueous ethanol. The liquid carrier is suitably sterile and pyrogen free.

The compositions may be in the form of liquids suitable for infusion or injection, or syrups, suspensions or solutions, as well as solid forms such as capsules, tablets, or reconstitutable powders.

Constructs for use in the vaccines of the invention may be prepared by various means as will be understood in the art, ranging from modification of available constructs such as the wild-type virus using recombinant DNA technology or by synthetic means. Recombinant DNA techniques include site directed mutagenesis, optionally involving PCR amplification as illustrated hereinafter.

As illustrated hereinafter, recombinant vaccinia virus was constructed which expressed the structural genes of VEE as produced by a modified form of TC-83. The ability of the recombinant virus to elicit protective immune responses against virulent VEE disease was investigated.

In yet another embodiment, the vaccine further comprises a cytokine or an active fragment or variant thereof. The cytokine may itself be incorporated into the vaccine formulation, or more suitably, the vector may include a coding sequence which means that the cytokine is co-expressed by the vector. Examples of suitable cytokines include interleukin 2 (IL-2) and interleukin 6 (IL-6).

A particularly suitable cytokine is interleukin 2 (IL-2), which may be expressed from for example a vaccinia virus recombinant. IL-2 is known to be responsible for the clonal expansion of antigen-activated T cells (Smith, (1984) Reviews in Immunology 2, 319–333).

Alternatively, antibody levels can be enhanced using other cytokines. For example, expression of IL-6 by vaccinia vectors has been shown to induce a high level of IgG, (Ruby et al, 1992 Vaccine Research 1, (4), 347–356), and IL-5 and IL-6 induced mucosal IgA responses to co-expressed influenza HA (Ramsay et al, (1994) Reproduction, Fertility and Development 6, 389–392).

The vaccine of the present invention may be used to treat humans or animals. In particular it may be given to horses, as a veterinary vaccine, to prevent infection, or as a prophylactic or therapeutic vaccine for humans.

The vaccine of the invention may be incorporated into a multivalent vaccine in order to increase the benefit-to-risk ratio of vaccination.

The dosage of the vaccines of the invention will depend upon the nature of the mammal being immunised as well as the precise nature and form of the vaccine. This will be determined by the clinician responsible. However in general, when using a virus vector such as a vaccinia virus vectors, dosages of the vector may be in the range of from $10^4$–$10^{12}$ pfu (pfu=particle forming units).

The vaccines of the invention will produce an immune response in test animals including the production of antibodies. These antibodies may be useful in passive vaccination programmes or in diagnosis of VEE virus disease. For diagnostic purposes, the antibodies may form part of a kit as is conventional in the art.

The invention will now be illustrated by way of Example with reference to the accompanying drawings in which FIG. 1 shows the construction of chimeric plasmids used for generation of recombinant vaccinia viruses;

Figure 2:
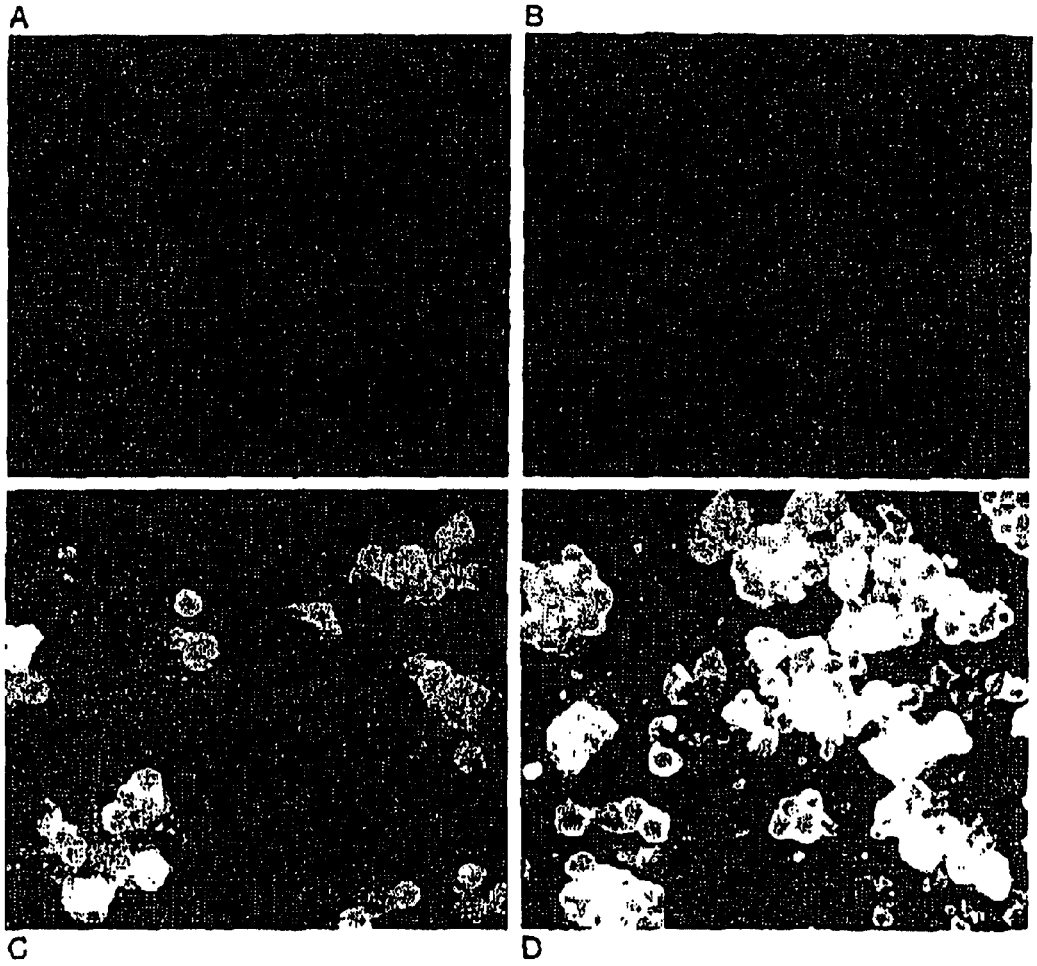
FIG. 2 shows the results of a immunofluoresence assay using polyclonal antiserum to TC-80.

In the Examples, relative protein levels were calculated from ELISA data using regression analysis performed by Minitab statistical analysis software (Minitab Inc., State College, Pa., USA). Serum antibody levels were compared by the two p, sample t test. Contingency tables were analysed by Fisher's exact test. P values of <0.05 were taken to be significant.

EXAMPLE 1

Alteration of the E2 Protein Sequence pTC-5A, a plasmid clone of cDNA encoding the structural genes of Venezuelan Equine Encephalitis virus, strain TC-83 was obtained from Dr. R, Kinney (Kinney et al, 1988, Journal of General Virology 69, 3005–3103). An Eco RI fragment containing the VEE cDNA was removed from PTC-SA and inserted into p1113 (Carroll, 1993, Ph.D. thesis, Faculty of Medicine, University of Manchester; FIG. 1a) which is a shuttle vector used for insertion of genes into the thymidine kinase locus of vaccinia with dominant selection of recombinant viruses based on resistance to mycophenolic acid (Falkner & Moss, 1988, Journal of Virology 62, 1849–1854). The resulting plasmid, pAB100, was mixed with Lipofectin™ (Life Technologies) and used to transfect CV-1 cells infected with vaccinia virus, strain WR. Recombinant viruses were designated WR100 and were subjected to three rounds of plaque-purification before preparation of stocks as described earlier (Mackett et al, 1985 DNA cloning (Volume II): a practical approach).

The sequence of VEE E2, strain TC-83, situated in pTC-5A, was altered by one nucleotide substitution from T to G as position 1053 as compared; to wild-type VEE TRD (Johnson et al. J. Gen. Virol. 1986, 67, 1951–1960). This resulted in an amino acid change from asparagine to lysine in the E2 protein when expressed from the vaccinia virus.

In order to perform this particular amino acid change, the following manipulations were carried out.

A cleavage site for restriction enzyme Nsi I occurs close to the site of the required nucleotide substitution. A second Nsi I site is situated about 500 bp upstream. Oligonucleotide primers were used to amplify the DNA sequence between the Nsi I sites using the Polymerase Chain Reaction (PCR). The downstream primer contained a nucleotide mismatch corresponding to the TRD sequence at this point.

The primer sequences are listed below. The Nsi I cleavage sites and the position of the substituted nucleotide are underlined.

Primer 1 Designated "Nsi 1" (SEQ ID NO:4)

5'GCC GAT GCA TGT GGA AGG C 3'

Primer 2 Designated "Nsi 2" (SEQ ID NO:5)

5'ATC TGA TGC ATC TGG CCATGT AAG GGC GCG TTA GCT TAT ACT CCT TAA ACA GC 3'

The PCR product was digested with Nsi I and used to replace the corresponding Nsi I fragment in PTC-SA, generating plasmid pAB101. The nucleotide sequence of the relevant region in pAB101 was obtained to verify the sequence alteration.

pAB101 was then digested with Eco R1 to remove the VEE 26S RNA coding sequence which was transferred to the vaccinia shuttle vector plasmid p1113. P1113 contains the selectable marker gpt which allows selection of recombinant vaccinia viruses. The plasmid constructed by the addition of the VEE sequence to p1113 was designated pAB102.

EXAMPLE 2

Substitution of 7.5K Promoter for a Synthetic Promoter in pAB102

A synthetic 7.5K vaccinia promoter was designed, based upon work by Davison and Moss (supra.). Complementary oligonucleotides were designed with 5'Bam HI and 3'Eco RI ends. The oligonucleotides were annealed and ligated into the plasmid pT7Blue (available from AMS Biotechnology (UK) Ltd). The plasmid clone was digested with Bam HI and Eco RI and the DNA fragment containing the synthetic promoter was isolated and cloned into the plasmid pAB102 which had been cut with the same enzymes. This resulted in the generation of plasmid pAB103 (FIG. 1) which contains the synthetic promoter upstream of the VEE 26S RNA coding sequence. Vaccinia WR strain was transformed with PAB103 to produce the recombinant vaccinia virus WR103.

The sequence of the oligonucleotides used is given below. Substitutions in the 7.5K promoter sequence are given in bold type. Insertions are underlined. Oligonucleotide "tails" containing restriction enzyme cleavage sites are italicised.

5' ACG CGG ATC C
AA AAA TTG AAA AAC TAG CTT AAA AAT TGA
AAA ACT ATT CTA ATT TAT TGC ACG AAT TCC G 3'

Oligo 2 Designated "7.5KR2"

This is the reverse complement of 7.5KF2.

The amount of VEE proteins produced by the recombinant virus WR103 was measured using enzyme linked immunoabsorbant assay (ELISA).

EXAMPLE 3

Analysis of Protein Expression

VEE viral proteins were visualised by indirect immunofluorescence of infected CV-1 cells. CV-1 monolayers (25 $cm^2$) were infected with virus at a multiplicity of 2 p.f.u. per cell. At 24 hours post infection, cells were scraped into the growth media and washed once with phophate-buffered saline (PBS) containing 0.1% bovine serum albumin. Cells were spotted onto slides, air-dried and fixed in acetone. Binding of mouse polyclonal antiserum raised against VEE strain TC-80 (provided by Dr. A. D. T. Barrett, University of Texas) was detected with fluorescein isothiocyanate-conjugated goat anti-mouse IgG (Amersham International plc).

Examination of cells infected with WR100 or WR103 showed that WR103-infected cells fluoresced more brightly than the WR100-infected cells (FIG. 2).

Quantification of VEE viral protein expression was carried out using an enzyme-linked immunosorbent assay (ELISA). CV-1 monolayers (150 $cm^2$) were infected with virus at a multiplicity of 10 p.f.u. per cell and harvested at 24 hours post infection by scraping into the growth media. Cells were washed once in PBS and resuspended in T9 buffer (10 mM Tris.HCl; 1 mM EDTA; pH 9.0). Samples were frozen, thawed and sonicated for 1 minute in a sonicating bath. Cells debris was pelleted for 5 minutes at 1800 g and the supernatant was centrifuged for 30 minutes at 10,000×g. The supernatant was removed and stored at −70° C. The cell lysate preparation was diluted 1/30 in bicarbonate buffer (Sigma), 100 l volumes were added to wells of a microtitre plate and the antigen was allowed to bind at 37° C. for 1 hour. Lysates were replaced with 200 l/well of saline containing 10% formaldehyde. Plates were incubated at room temperature for 20 minutes, then washed 6 times with PBS, containing 0.1% Tween (PBST). Mouse polyclonal anti-TCBO was serially diluted in blocking solution (0.5% dried milk/PBST), added to wells, and the plates were incubated for 1 hour at 37° C. Plates were washed 3 times in PBST before addition of horseradish peroxidase-conjugated mouse specific antibody (diluted 1:1000 in blocking solution) and incubated for 1 hour at 37° C. Plates were washed 3 times more addition of ABTS in citrate buffer and incubation at room temperature for 1 hour. Colour development was measured at $A_{414}$.

Figure 3:
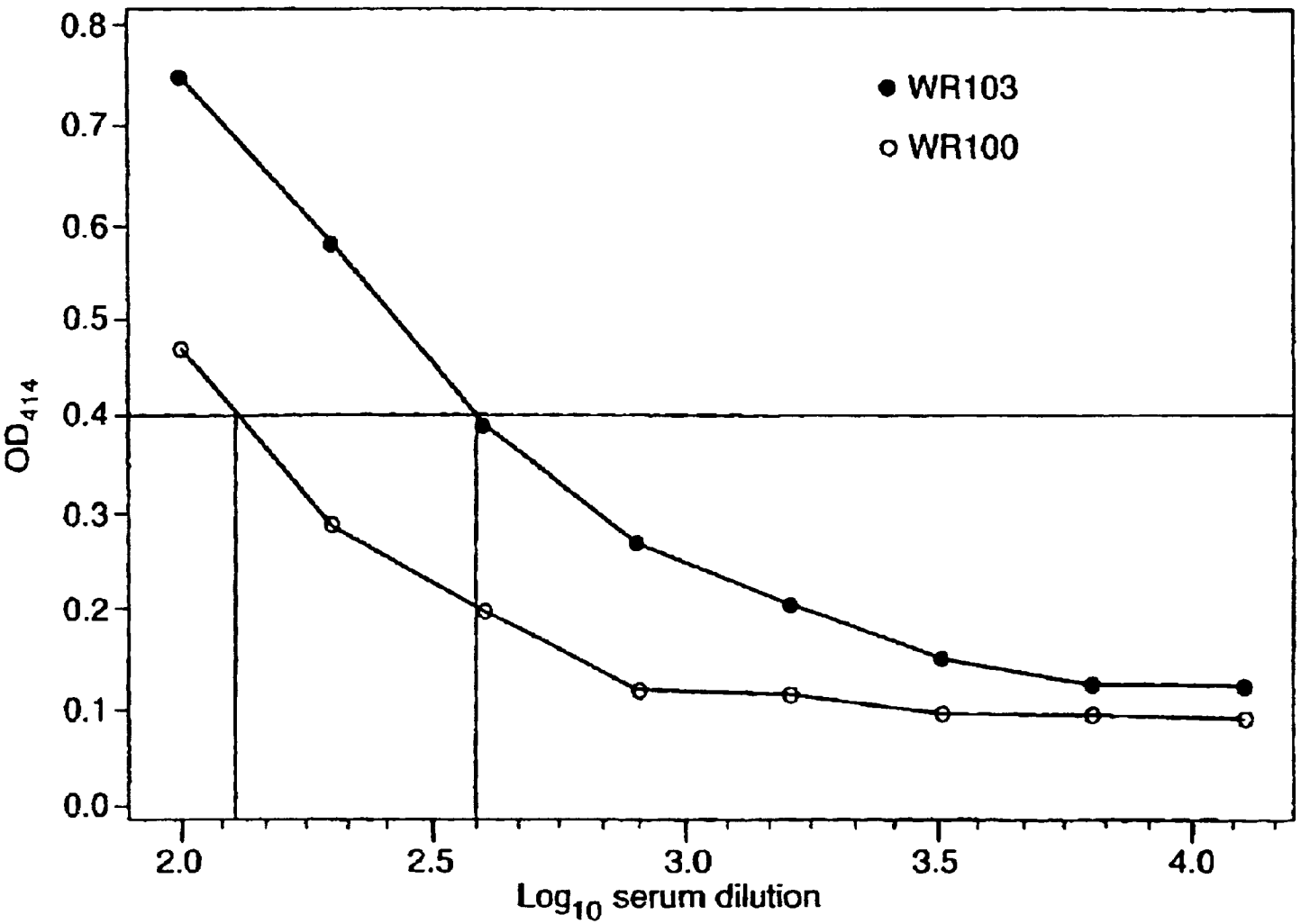
FIG. 3 is a graph showing the results of an experiment to quantify by ELISA the amount of VEE protein expressed by strains.

This quantification process revealed that WR103-infected cells contained 3.59-fold more VEE protein than WR100-infected cells (FIG. 3).

Quantification of vaccinia protein in these samples had demonstrated equivalent amounts in each (data not shown), so it must be assumed that the difference in VEE protein content is due to different expression levels of the encoded VEE cDNA.

EXAMPLE 4

Protective Effect of Vaccinia Recombinants

Groups (10) of female 6–8 week old Balb/c mice were inoculated with PUS or with $10^8$ p.f.u. of vaccinia viruses by intra-muscular injection, or with $10^5$ p.f.u. of TC-83 by subcutaneous injection. Serum was taken for measurement of immunoglobulins to VEE proteins.

The vaccinated mice were challenged with two different doses of virulent VEE strain TRD at 35 days idler immunisation. The survival rates after 14 days are presented in Table 2.

TABLE 2

| Strain | 10 pfu TRD | 100 pfu TRD |
|---|---|---|
| WR | 0/10 | 0/10 |
| WR100 | 1/10 | 2/10 |
| WR103 | 6/10 | 6/10 |
| No treatment | 0/10 | 0/10 |

WR100: Vaccinia/VEE recombinant
WR103: Vaccinia/VEE recombinant produced in Example 2 above.

These results show that genetic manipulation of the recombinant virus has improved the protection afforded by the construct. A significant improvement in protection of mice following subcutaneous challenge with TrD was seen when WR103 was used for vaccination, compared with WR100 ($P<0.05$, Table 2). WR100 protected up to 20% of mice whereas WR103 protected 60% of mice. There was not a significant difference between numbers of mice protected when challenge doses of 10 p.f.u. or 100 p.f.u. of TrD were used. The challenge dose had previously been titrated to show that 1 p.f.u. of TrD approximates to 2–3 $LD_{50}$ doses (data not shown).

EXAMPLE 5

Immunoassays

VEE virus-specific immunoglobulin in serum was measured by enzyme-linked immunoassay as follows. Wells of a microtitre plate were coated with purified TC-K3 at 37° C. for 1 hour. Serum was diluted serially in blocking solution and allowed to bind to antigen-coated wells overnight at 4° C. Plates were washed 3 times and incubated with horseradish peroxidase-conjugated anti-mouse immunoglobulin at 37° C. for 1 hour. Plates were washed and incubated with TMB substrate for 20 minutes before measurement of colour development at $A_{450}$.

Figure 4:
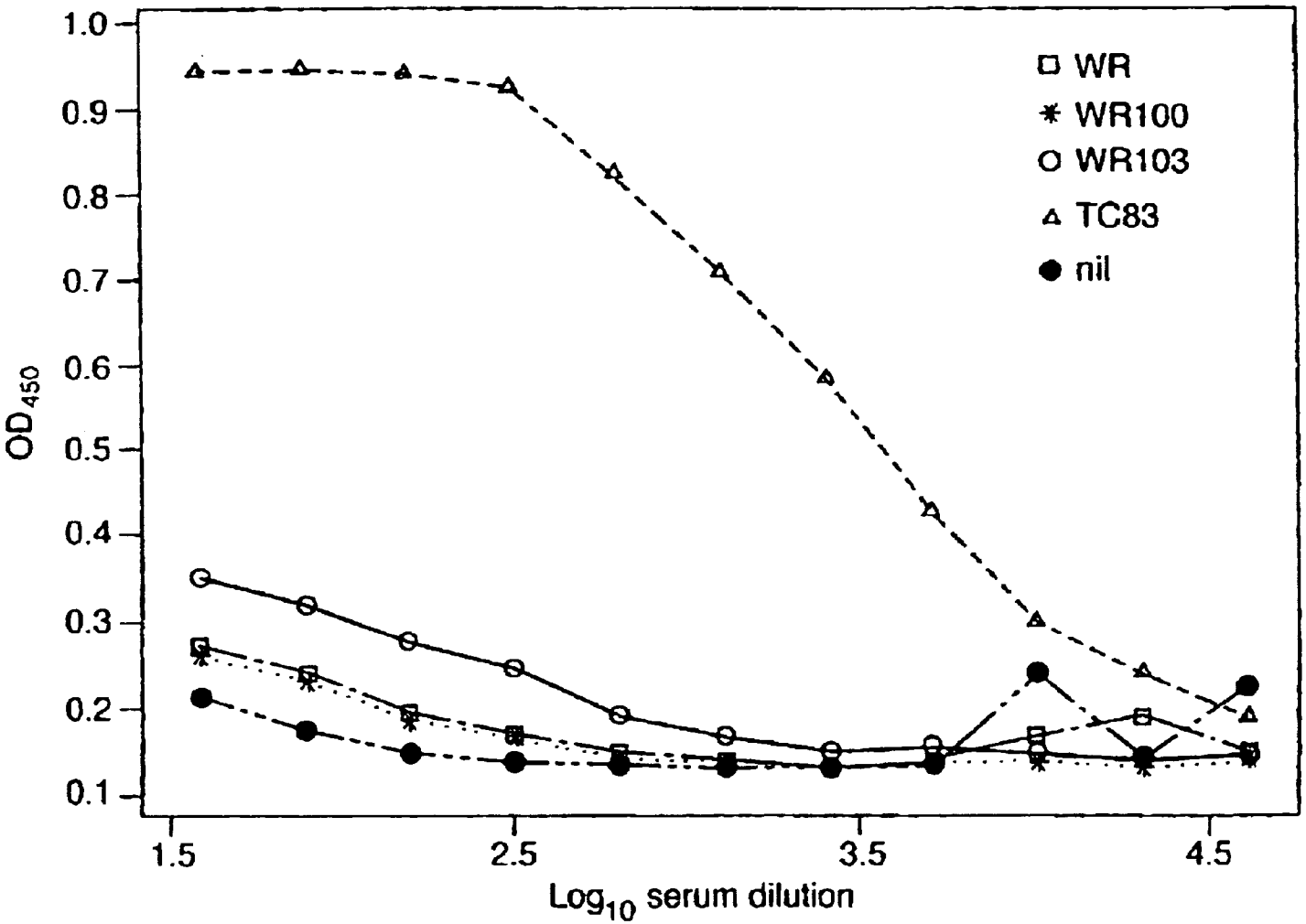
FIG. 4 is a graph showing the results of an experiment to find the level of anti-VEE IgG in animals vaccinated with various strains of the invention.

All vaccinia-inoculated mice responded to the vaccination by the detection of immunoglobulin to vaccinia virus in serum (data not shown). Immunoassay to measure TC-83 antibody failed to detect anti-VEE IgG in WR100 samples. WR103 samples contained a detectable level of anti-VEE antibody although this was substantially lower than the amount found in serum from mice vaccinated with TC-83 (FIG. 4).

Neutralising antibody was measured by a plaque reduction test. Serum (1.0 μl) was incubated with TC-83 (50 μl) and maintenance medium (140 μl) for 1 hour at room temperature. Maintenance medium (800 μl) was added and the suspension was used to infect confluent monolayers of BHK-21 cells grown in 6-well plates. Plates were incubated at 37° C. for 3 days. A 50% reduction in the number of plaques per well, compared to control wells, was indicative of the presence of neutralising antibody.

Neutralising antibody to TC-83 was found in serum from mice vaccinated with TC-83 but was not detected in serum from mice vaccinated with WR100 or WR103 (data not shown). Although neutralising antibody is usually found in mice which are protected against VEE challenge, protection hits previously been reported in the absence of delectable neutralising antibody (Kinney et al, 1988a, Journal of Virology 62, 4697–4702).

SEQUENCE LISTING

```
<160> NUMBER OF SEQ ID NOS: 6

<210> SEQ ID NO 1
<211> LENGTH: 33
<212> TYPE: DNA
<213> ORGANISM: Venezuelan equine encephalomyelitis virus

<400> SEQUENCE: 1

taaaagtaga aaatatattc taatttattg cac                                33


<210> SEQ ID NO 2
<211> LENGTH: 33
<212> TYPE: DNA
<213> ORGANISM: Artificial Sequence
<220> FEATURE:
```

-continued

```
<223> OTHER INFORMATION: Description of Artificial Sequence:
      Substitution mutation

<400> SEQUENCE: 2

taaaaattga aaatacattc taatttattg cac                                33


<210> SEQ ID NO 3
<211> LENGTH: 33
<212> TYPE: DNA
<213> ORGANISM: Artificial Sequence
<220> FEATURE:
<223> OTHER INFORMATION: Description of Artificial Sequence:
      Substitution mutation

<400> SEQUENCE: 3

taaaaattga aaatatattc taatttattg cac                                33


<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 4

gccgatgcat gtggaaggc                                                19


<210> SEQ ID NO 5
<211> LENGTH: 53
<212> TYPE: DNA
<213> ORGANISM: Artificial Sequence
<220> FEATURE:
<223> OTHER INFORMATION: Description of Artificial Sequence: Primer

<400> SEQUENCE: 5

atctgatgca tctggccatg taagggcgcg ttagcttata ctccttaaac agc          53


<210> SEQ ID NO 6
<211> LENGTH: 70
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 6

acgcggatcc aaaaattgaa aaactagctt aaaaattgaa aaactattct aatttattgc   60

acgaattccg                                                          70
```

What is claimed is:

1. A vaccine for the therapeutic or prophylactic immunisation against Venezuelan Equine Encephalitis (VEE) virus, said vaccine comprising a vector which includes a sequence which encodes an attenuated form of said virus which is capable of producing a protective immune response, wherein the said sequence is such that the amino acid at position 7 in the E2 protein of VEE is lysine.

2. A vaccine according to claim 1 wherein the attenuated form of said virus comprises a derivative of the TC-83 construct.

3. A vaccine according to claim 2 wherein the vector comprises a virus vector.

4. A vaccine according to claim 3 wherein the virus is selected from an attenuated virus.

5. A vaccine according to claim 3 wherein the virus is selected from vaccinia, adenovirus or herpes simplex virus (HSV).

6. A vaccine according to claim 5 which comprises an attenuated vaccinia virus.

7. A vaccine according to claim 6, wherein expression of the said attenuated VEE virus is under the control of a synthetic 7.5K vaccinia promoter which has been subject to mutation which Increases the level of VEE virus protein production as compared to the wild-type 7.5K promoter.

8. A vaccine according to claim 7 wherein the said 7.5K promoter comprises the sequence TAAAAATTGAAAATACATTCTAATTTATTGCAC (SEQ ID No 2).

9. A vaccine according to claim 1 which comprises a vector which includes a nucleotide sequence which encodes a further immunogenic peptide, and is able to express said sequence when administered to a mammal.

10. A vaccine according to claim 1 which further comprises a cytokine or an active fragment or variant thereof, or a vector which comprises a nucleotide sequence which encodes a cytokine or an active fragment or variant thereof.

11. A vaccine according to claim 10 which comprises a vector which comprises a nucleotide sequence which encodes a cytokine or an active fragment or variant thereof.

12. A vaccine according to claim 10 wherein the cytokine is an interleukin.

13. A vaccine according to claim 10 wherein the interleukin is selected from human IL-2 or human IL-6.

14. A pharmaceutical composition comprising a vaccine as defined in claim 1 and a pharmaceutically acceptable carrier or excipient.

15. A method for producing a protective immune response against VEE virus in a mammal, which method comprises administering to said mammal, a vaccine according to claim 1.

16. A method according to claim 15 wherein the mammal is either a human or a horse.

*17. A method for producing a protective immune response against Venezuelan Equine Encephalitis (VEE) virus in a mammal, which method comprises administering to said mammal, a vaccine against VEE virus comprising a vector which comprises a sequence encoding the N-terminal 19 amino acids of the E2 protein of VEE, said vaccine being capable of producing a protective immune response, wherein the said sequence is such that the amino acid at position 7 in the E2 protein is lysine, wherein the vector encodes an attenuated form of said virus which is capable of producing a protective immune response.*

*18. A method of claim 17 wherein the fragment encodes the N-terminal 25 amino acids of the E2 protein of VEE and the amino acid at position 7 in the E2 protein is lysine.*

*19. A method according to claim 17 wherein the attenuated form of said virus comprises a derivative of the TC-83 construct.*

*20. A method according to claim 17 wherein the vector comprises a virus vector.*

*21. A method according to claim 20 wherein the virus vector is selected from an attenuated virus.*

*22. A method according to claim 21 wherein the attenuated virus is a virus selected from vaccinia, adenovirus or herpes simplex virus (HSV).*

*23. A method according to claim 22 wherein the attenuated virus is an attenuated vaccinia virus.*

*24. A method according to claim 23, wherein expression of the sequence encoding the N-terminal 19 amino acids of the E2 protein of VEE is under the control of a synthetic 7.5K vaccinia promoter which has been subject to mutation which increases the level of VEE virus protein production as compared to the wild-type 7.5 promoter.*

*25. A method according to claim 24 wherein the 7.5K promoter comprises the sequence*

*TAAAAATTGAAAATACATTCTAATTTATTGCAC (SEQ ID NO: 2).*

*26. A method according to claim 17 wherein the vaccine further comprises a vector which includes a nucleotide sequence which encodes a further immunogenic peptide, and is able to express said sequence when administered to a mammal.*

*27. A vaccine for the therapeutic or prophylactic immunisation against Venezuelan Equine Encephalitis (VEE) virus, said vaccine comprising a virus vector which comprises a sequence encoding the N-terminal 19 amino acids of the E2 protein of VEE, said vaccine being capable of producing a protective immune response, wherein the said sequence is such that the amino acid at position 7 in the E2 protein is lysine,*

*said vaccine further comprising a cytokine or an active fragment or variant thereof, or a vector which comprises a nucleotide sequence which encodes a cytokine or an active fragment or variant thereof.*

*28. A vaccine according to claim 27 which comprises a vector which comprises a nucleotide sequence which encodes a cytokine or an active fragment or variant thereof.*

*29. A vaccine according to claim 27 wherein the cytokine is an interleukin.*

*30. A vaccine according to claim 27 wherein the interleukin is selected from human IL-2 or human IL-6.*

*31. A pharmaceutical composition comprising a vaccine as defined in claim 27 and a pharmaceutically acceptable carrier or excipient.*

*32. A method for producing a protective immune response against VEE virus in a mammal, which method comprises administering to said mammal, a vaccine according to claim 27.*

*33. A method according to claim 32 wherein the mammal is either a human or a horse.*

*34. A method according to claim 17 wherein the mammal is either a human or a horse.*

* * * * *